United States Patent [19]

Wassenhoven

[11] Patent Number: 4,891,974
[45] Date of Patent: Jan. 9, 1990

[54] METHOD AND APPARATUS FOR DETERMINING CHARACTERISTICS OF STAPLE FIBER YARNS

[75] Inventor: Heinz-Georg Wassenhoven, Monchen-Gladbach, Fed. Rep. of Germany

[73] Assignee: W. Schlafhorst & Co., Fed. Rep. of Germany

[21] Appl. No.: 249,349

[22] Filed: Sep. 23, 1988

[30] Foreign Application Priority Data

Sep. 26, 1987 [DE] Fed. Rep. of Germany ....... 3732513

[51] Int. Cl.⁴ .............................................. G01L 5/04
[52] U.S. Cl. ....................................... 73/160; 73/847; 57/264; 57/265; 364/40; 364/563
[58] Field of Search .......................... 73/160, 788, 847; 57/264, 265; 364/470, 551.07, 563

[56] References Cited

U.S. PATENT DOCUMENTS

3,377,853 4/1968 Carter ................................... 73/160
3,919,886 11/1975 Chambley .............................. 73/160
4,648,054 3/1987 Farah et al. ............................ 73/160

Primary Examiner—Stewart J. Levy
Assistant Examiner—Michele Simons
Attorney, Agent, or Firm—Shefte, Pinckney & Sawyer

[57] ABSTRACT

An apparatus and method for determining characteristics of staple fiber yarn by measuring the change in the yarn diameter after twisting or untwisting of the yarn. The yarn thickness of a length of yarn is measured during a first measuring process and subsequently, by a second measuring process after the twist is released. The two series of values of yarn thickness or diameter can then be compared with one another to determine certain characteristics of the sampled yarn.

26 Claims, 5 Drawing Sheets

METHOD AND APPARATUS FOR DETERMINING CHARACTERISTICS OF STAPLE FIBER YARNS

BACKGROUND OF THE INVENTION

The present invention relates to a method and apparatus for determining characteristics of staple fiber yarn.

Staple fiber yarns are produced by various spinning processes, resulting in differing structures and characteristics. One type of spinning is open end spinning, which produces a yarn having a main strand covered by wrapper fibers that imposes constrictions of various lengths randomly disposed over the length of the yarn. Another type of spinning is air spinning, which produces a yarn having fibers in a somewhat parallel orientation with strength provided by wrapper fibers. Yet another type of spinning is friction spinning, which produces a yarn having a somewhat random fiber orientation.

Because of the different characteristics obtained by the different spinning processes, it is advantageous to know the characteristics of a yarn for appropriate further processing and appropriate fabric usage.

SUMMARY OF THE INVENTION

The present invention provides a method and apparatus for determining the characteristics of yarns produced by various staple yarn spinning processes so that the most appropriate additional processing and the most appropriate fabric usage can be determined. In particular, the present invention provides a method and apparatus capable of comparing a yarn produced by a new spinning process with yarns produced by conventional spinning processes to determine the applicability of the yarn for commercial use. In accordance with the method of the present invention, the diameter of a yarn segment of given length is measured at various points along the length of the segment and the diameter values are stored. The yarn segment is then twisted or untwisted by a predetermined amount and the diameter of the segment is meansured at the same points at which the diameter was measured during the first measurement process. These diameter values are also stored in an appropriate device, such as a computer, which can then display a comparison of the diameter values from the first and second measurement series, thereby enabling one to determine particular characteristics of the yarn based on the comparison of diameter values.

In another aspect of the present invention, an opto-electric device can be used to measure the shadow cast by a yarn segment of given length during a first measurement series. The yarn segment can then be twisted or untwisted by specified amount and a second measurement series conducted by the opto-electric device. A comparison of the shadow measurements from the two measurement series will then provide information concerning the character of the yarn segment.

If the yarn segment is untwisted by a specified amount after the first measurement series and the yarn is, for example, a ring spun yarn, the diameter of the yarn segment will typically significantly increase. If the yarn segment is of the open spinning type yarn, there will generally be no increase in the yarn segment diameter at those points at which the yarn segment is covered by wrapper yarns of relatively large size. At those particular points, the diameter typically remains the same after the untwisting or, in fact, may even decrease due to the constricting effect of the wrapper yarns, since the constricting effect tends to increase due to the untwisting process.

In addition to the shadow measuring process, the present invention comprehends the use of other measurement processes such as, for example, measurement processes based on the reflection principle.

The measurement of the yarn segment diameter need not be simultaneously conducted at all the measurement points of the segment. In fact, in many instances, such simultaneous measurement is not recommended. Preferably, the diameter is sequentially measured at each measurement point over the length of the segment.

The recording of the diameter values can be accomplished by a printer coupled to the diameter sensing device. Preferably, a computer performs the tasks of recording, displaying, storing and evaluating the diameter values.

In accordance with the apparatus of the present invention, the yarn segment is stretched between two grippers, one gripper applying tension to one end of the segment and the other gripper holding the other end of the segment at a predetermined position and being rotatable about the segment axis to impart twisting or untwisting movement to the segment.

The imparting of a twisting or untwisting movement to the segment between the two measurement series may involve the imparting of an untwisting motion of predetermined duration to the segment so that the pre-existing twist of the segment is decreased or eliminated. Generally, the segment diameter increases during such untwisting motion. It is also possible to impart additional twisting to the segment and then to untwist the segment. Also, it is possible to first untwist the segment and then to twist the segment before conducting the second measurement series.

Since each type of yarn behaves differently during such twisting or untwisting, it is possible to determine certain characteristics of the yarn through the method and apparatus of the present invention. To determine the extent of twisting or untwisting to be imparted to the yarn segment, the fineness of the yarn, the existence of twisting already imparted by the yarn production process and the type of yarn material can be taken into account.

For example, if the twist characteristic of the yarn is known, an untwisting motion can be imparted to the yarn so that the yarn is substantially without twist when the second measurement series is conducted. Typically, the yarn lengthens due to the untwisting but it is not necessary to determine the change of length of the yarn.

If the twisting or untwisting movement of the yarn is determined in accordance with the above-mentioned yarn parameters, the comparison of other segments of the same type of yarns is facilitated.

Preferably, the yarn is released from its pre-existing twist prior to the second measurement series. However, in this regard, it is not always necessary to observe the degree to which the segment was already twisted.

Also, once the segment has been rendered essentially twist-free, it is preferable to impart a predetermined number of twists or counter-twists to the segment so that the number of twists in the segment is precisely known at the time the second measurement series is conducted.

In another aspect of the present invention, a third measurement series is conducted after the segment has received a predetermined number of twists after the second measurement series. It is then possible to compare the diameter values from the three measurement series and thereby determine particular characteristics of the yarn segment. The differences between the values of each measurement series typically become clearer when a third measurement series is conducted.

The degree of tension to which the segment is subjected during the measurement process can vary. For example, segments of yarn of a certain type can be measured while in a tension-free condition. On the other hand, segments of yarn of another type can be placed in tension without significantly influencing the diameters measured thereon. Thus, in one aspect of the present invention, the segment is subjected to a tension of predetermined amount during the measurement series. This tension need not be a large tension. If the segment is tensioned in a horizontal direction during the measurement series, the tension need only be sufficient to insure that no sags, dips or snarls occur. Thus, the predetermined tension can be, for example, imparted by a weight connected to the segment.

It is possible to fully release the segment from its pre-existing twist even if the degree of twisting is not known if one observes the lengthening of the segment during the untwisting of the segment and conducts the second measurement series only when the lengthening of the yarn has ceased. The lengthening of the yarn can also be numerically determined by the use of, for example, a scale.

In one embodiment of the apparatus of the present invention, the measurement sensor is moved parallel to the yarn during the measurement series. However, it is also contemplated that the sensor can be held in one place while the yarn is moved relative thereto. If the sensor is moved along the length of the segment, a printing device coupled to the sensor can immediately display a plot of the diameter values. However, it is preferable that the sensor be an opto-electric sensor which operates in accordance with the above-mentioned shadow principle.

Preferably, the amount of positive or negative twist imparted to the segment as well as the change in length of the segment is measured as well.

In segments of the same type of yarn, the change of length of the yarn generally increases, the more the yarn is untwisted. However, if yarns produced by different methods are compared, it can be seen that the amount by which the yarn segments change in length varies considerably when subjected to the same degree of twisting or untwisting. This enables one to pinpoint the characteristics of the various yarns from which the segments are taken.

If the segment diameter is measured at a number of selected points along the segment length so as to create a plot of these values connected by a continuous curve, it is preferable that the distance between each diameter measuring point be in the range of approximately 0.5 to 1 millimeter. Otherwise, the continuous curve may be too imprecise.

If the measurement of the diameter values is accomplished by digital equipment, certain advantages are obtained. For example, the sensor can be programmed to run without interruption over the length of the segment and to sense the segment diameter at each of the preselected points. On the other hand, the sensor can be programmed to come to a stop over each measurement point.

If the sensor is run uninterruptedly over the length of the segment, the computer can be programmed to select diameter values at a given interval such as, for example, every 0.5 millimeters. The length of a segment measured by such a measurement process can be, for example, 400 to 500 millimeters.

It is preferable that the plot of the diameter values from the two measurement series be displayed on the same chart. This facilitates comparison of the diameter values and especially facilitates the observation and interpretation of points at which the diameter value plots intersect. Furthermore, it is especially advantageous to adjust the length of the plot of the diameter values from the second measurement series so that the two diameters values measured for each point are in vertical alignment. As discussed above, the segment is generally longer when the second measurement series is conducted so that each measurement point is slightly offset from the position at which the first measurement series was conducted. Conversely, the plot of the diameter values from the first measurement series can be correspondingly lengthened so that the two diameter values for each given measurement point are vertically aligned on the chart.

The present invention provides information by which one can determine that the segment is from a type of yarn covered by a wrapper yarn; for example, if the diameter values recorded during the second measurement series (after the segment has been imparted with a negative twist) are less at certain points than were recorded during the first measurement series, then the yarn is likely to be of the wrapper yarn type. This decrease in the diameter at certain measurement points can be detected by plotting the diameter values from the first and second measurement series on the same chart and noting where the two plots intersect or overlap. In those regions where the plots overlap, the diameter has decreased. As can be understood, the length of the overlap corresponds to the length of the wrapper yarn portion of the segment. Accordingly, it is possible to determine the length of the wrapper yarn portion of the segment.

Other characteristics of the segment can be determined by calculating the number of wrapper yarn portions of the segment, their individual lengths, their average lengths, and the total cumulative lengths over the entire segment.

With information obtained by using the method and apparatus of the present invention, one can determine that the segment derives from a hard yarn type suitable for use in fabric with a hard feel and a correspondingly smooth outer surface. For example, if the comparison of the diameter values reveals relatively little change in the average diameter values between the first and second measurement series, these yarns have the characteristics of worsted wool and are thus suitable for use in corresponding worsted wool textiles.

Similarly, the method and apparatus of the present invention enable one to determine that the segment is of a fleece type yarn and thus suitable for use in fabric with a soft feel and a soft look as well as for use in knitted fabrics. For example, if the comparison of the diameter values from the two measurement series reveals a comparatively large change in the average diameter or a large change in the highest diameter values, the yarn is probably fleece type yarn. Yarns from ring spinning machines typically reveal such characteristics when evaluated according to the present invention.

It is to be understood that the evaluation of the yarn provided by the present invention is only of a rough, general type.

Briefly described, the apparatus of the present invention includes gripping means for gripping one end of the segment and another gripping means spaced from the first gripping means for gripping the other end of the segment. One of the gripping means is movable in the axial direction of the segment while the other gripping means is not axially movable relative to the segment. Also, one of the gripping means, preferably the one that does not move axially, is rotatable about the segment axis to impart a twist to the segment. A sensor movable along the length of the segment is coupled to a computer having storage and display capabilities for displaying the measured diameter values.

The segment is held in tension by the gripping means while the sensor measures the diameter values. As desired, the segment can be oriented in a vertical or a horizontal orientation during the measurement series.

In another embodiment of the invention, the sensor is stationary and the segment is moved thereby to obtain the diameter values. However, it is to be noted that a movable sensor is preferred.

A conventional personal computer can be readily adapted for use in the present invention. Preferably, the computer is coupled to a monitor and a printer.

The comparison of the diameter values can be displayed in various forms by the computer. For example, the computer can compute and display a plot showing the change in diameter values for each given measured point along the segment. As another example, the average value from each measurement series can be compared either graphically or numerically. In any event, the change in diameter values for a given point is a significant piece of evidence regarding the characteristic of the segment.

In another aspect of the present invention, one of the gripping means can be coupled to a rotation counter and the other gripping means can be coupled to a change in length indicator. Additionally, both the rotation counter and change of length indicator can be coupled to the computer.

The tension assembly including the gripping means is preferably provided with a weight means which places a constant tension on the segment. This can be accomplished, for example, by a weight connected to one of the gripping means. If the segment is horizontally oriented, the weight can be connected to the gripping means by a cord running over a pulley.

In another aspect of the present invention, a support bar oriented parallel to the segment provides a guide for moving the sensor along the segment. Additionally, a second rod which is rotatably coupled to the sensor to draw the sensor along the guide bar can also be provided. The rotations of the second bar can be monitored to control the movement of the sensor along the guide bar.

Preferably, the computer is programmed to display the diameter values of the first measurement series immediately after it has been conducted. Additionally, the computer is preferably programmed to calculate and display the change in length of the segment resulting from the twist imparted between the two measurement series.

In another aspect of the invention, the computer is preferably programmed to display additional information concerning the segment such as type of material, the segment length, the yarn count, the source of the yarn, and the spin process by which the yarn is produced. When such information is displayed together with the diameter values and information obtained therefrom, a reliable and fairly detailed picture of the yarn segment is provided which can be beneficially used to compare the yarn with other types of yarn.

Further features and advantages of the present invention will be apparent from the accompanying drawings and the following detailed description of the preferred embodiment.

DETAILED DESCRIPTION OF PREFERRED EMBODIMENTS

Figure 1A:
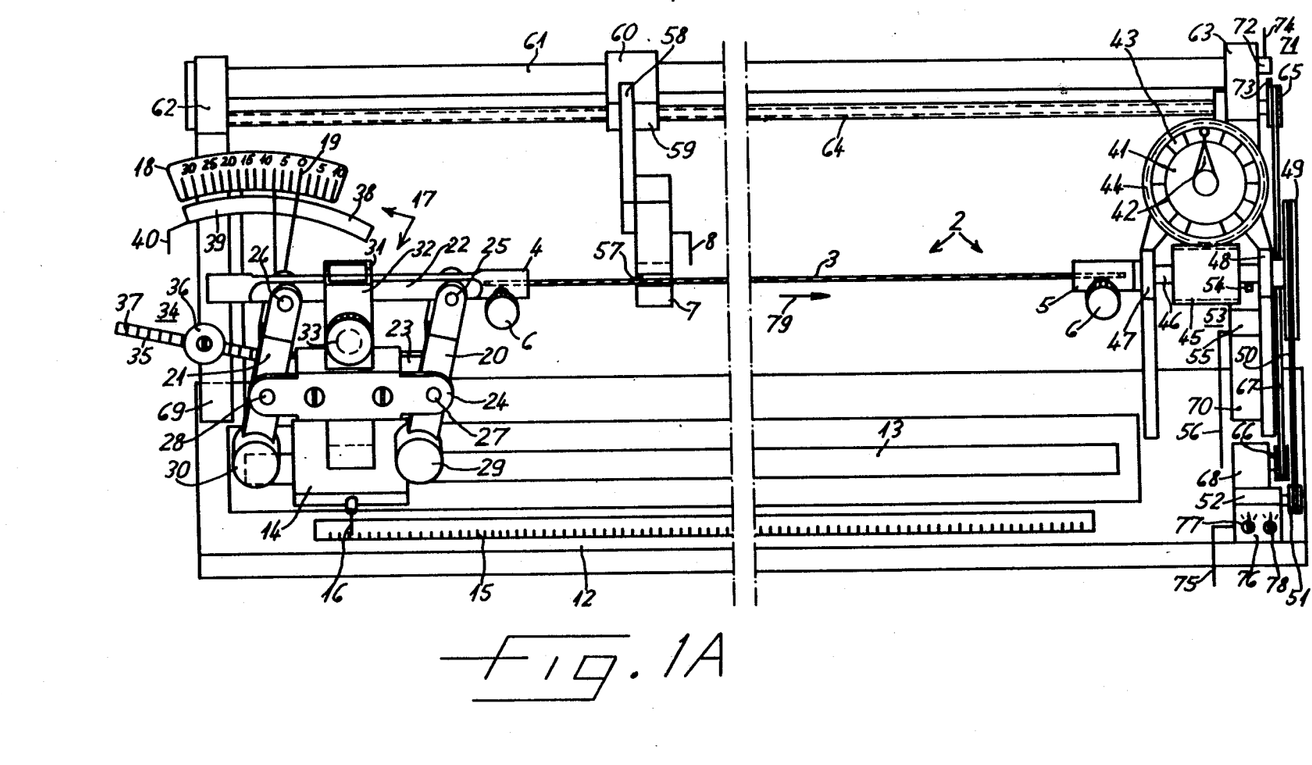
FIG. 1 is a schematic representation of an apparatus according to the preferred embodiment of the present invention.
Figure 1B:
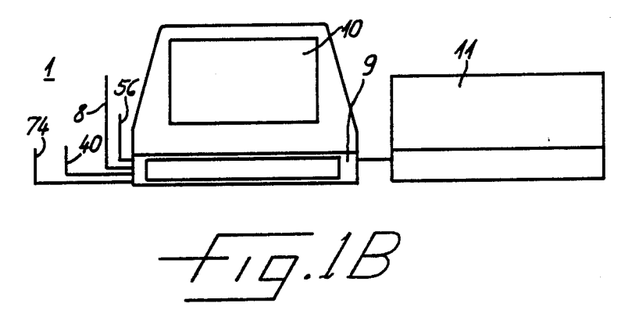

As shown in FIG. 1, the apparatus 1 of the present invention for measuring and testing includes a yarn tensioning apparatus 2 for tensioning a yarn segment 3 of a given length which, by way of example, is four hundred millimeters. It has been found that yarn lengths from four hundred to five hundred millimeters are especially suitable for measuring with this apparatus. The yarn tensioning apparatus 2 includes a first yarn gripper 4 and a second yarn gripper 5. Both grippers have receiving slots (not shown) for receiving one end of the yarn segment. A transversely movable bolt 6 on each yarn gripper is movable to engage and secure the yarn end in each receiving slot of the yarn grippers 4 and 5. The first yarn gripper 4 is movable in the axial direction of the yarn while the second yarn gripper 5 is rotatable about the yarn axis.

A sensor 7 is positioned near the tensioned yarn segment 3 and is adapted to measure the yarn thickness or, respectively, the yarn diameter over the length of the yarn. The sensor 7 is connected by a cable 8 to a computer 9 which has data storage capability. A suitable computer is, for example, any one of the commercially available personal computers. A monitor 10 and a printer 11 are operatively coupled to the computer 9. The computer 9 is adapted to store the yarn measurements provided by the sensor 7.

The yarn tensioning apparatus 2 also includes a base plate 12 and a guide 13 mounted thereon. Preferably, the guide 13 is of dovetail type. A support leg 14 on the first yarn gripper 4 is provided with a dovetail (not shown) which mates with and is guided along the guide 13. A length scale 15 is mounted on the base plate 12 slightly below and along the length of the guide 13. A pointer 16 mounted on the support leg 14 indicates the yarn length on the scale 15 as the support leg 14 is moved along the length of the guide 13.

The first yarn gripper 4 also includes a yarn length measuring device 17 of special construction. The yarn length measuring device 17 includes a scale 18 on which a pointer 19 indicates the length differences of the yarns 3 which appear during changes in the yarn twists. The yarn length measuring device 17 also includes two pivoted arms 20 and 21 pivotally coupled to a cross arm 22 and pivotally coupled to a pair of yoke halves 23 and 24. The yoke halves 23 and 24 are coupled to the support leg 14. Pivot pins 25 and 26 pivotally connect the pivoted arms 20 and 21, respectively, to the cross arm 22 and pivot pins 27 and 28 pivotally connect the pivoted arms 20 and 21, respectively, to the yoke halves 23 and 24. A pair of counterweights 29 and 30 are coupled to the pivoted arms 20 and 21, respectively, on the lower end of each arm opposite the end connected to the cross arm 22. The pointer 19 is mounted on the pivoted arm 21. Thus, the cross arm 22, the portions of pivoted arms 20 and 21 between cross arm 22 and the yoke halves 23 and 24 form a parallelogram.

By virtue of the parallelogram relationship of the pivoted arms, the pointer 19 can be set to the zero mark on the scale 18 by movement of the support leg 14 along the guide 13. If the yarn length measuring device 17 is not needed, the cross arm 22 can be held against movement by rotating the bolt 33 to move a pair of opposed jaws 31, 32 towards each other to thereby grip the cross arm 22 therebetween.

The yarn tensioning apparatus 2 also includes a yarn tension setter 34 having a lever 35 projecting perpendicularly from the pivoted arm 21 with a weight 36 adjustable along the length thereof. The lever 35 is marked with a scale 37 which indicates the yarn tension which has been set.

An arcuate strip 38 is coupled to the pointer 19 and moves with it. The arcuate strip 38 covers or uncovers a photocell 39 in response to the movement of the pointer 19. The photocell 39 is supplied with light from a light source (not shown) and is connected through a lead 40 with the computer 9.

The second yarn gripper 5 is operatively coupled to a rotation counter 41. The rotation counter 41 includes a non-moving pointer 42 and a rotatable scale 43. The scale 43 is coupled to a worm gear 44 which is threadably engaged by a worm screw 45. The worm screw 45 is mounted to a shaft 46 which is rotatably supported by posts 47 and 48. One axial end of the shaft 46 is coupled to the second yarn gripper 5 and the other axial end is coupled to a belt pulley 49. The posts 47 and 48 also rotatably support the worm gear 44 and are mounted to the base plate 12. An endless belt 50 operatively couples the pulley 49 with a second pulley 51 which is drivingly connected to the shaft of a motor 52.

The second yarn gripper 5 also includes a second rotation counter 53 having an electromagnetic sensor 55 which senses the rotation of a ferro-magnetic plug mounted to the shaft 46 for rotation therewith. The sensor 55 senses an impulse each time a peg 54 rotates one revolution. The sensor 55 is coupled by a lead 56 to the computer 9.

The sensor 7 also includes an opto-electric sensor of conventional construction having a measuring slot 57 for receiving the yarn 3 therein. A light source and a light sensitive element are positioned in opposed relationship on either side of the measuring slot 57 with the yarn 3 therebetween. The sensor 7 also includes a support 58 movable along the axial length of the yarn 3. The support 58 includes a spindle mount 59 coupled to a sleeve bearing 60. The sleeve bearing 60 is movable along a rod 61 with virtually no free play. The spindle mount 59 is secured against turning by its connection with the sleeve bearing 60. The spindle mount 59 is driveable axially along the rod 61 by a spindle 64. The spindle 64 is rotatably supported by a post 62, 63 at each respective axial end. The posts 62 and 63 are connected by legs 69 and 70 with the base plate 12. A pulley 65 is coupled to one axial end of the spindle 64. The pulley 65 is connected by a pulley 67 with another pulley 66 which is attached to the shaft of a motor 68 for driving movement therefrom.

The yarn tensioning apparatus 2 also includes a measuring device 71 having a spindle rotation counter 72. The counter 72 comprises an electromagnetic sensor which senses the rotation of a magnetic peg 73 fixed to the periphery of the pulley 65. A lead 74 connects the measuring device 72 to the computer 9.

The motors 52 and 68 are connected by a lead 75 to a control box 76, which supplies the motors with power from an electrical power source. Controls 77 and 78 can be operated to switch the motors 52 and 68, respectively, from forward to reverse.

FIG. 1 shows the yarn segment 3 in tension. As shown in FIG. 1, the support legs 14 have been moved along the guide 13 to bring the pointer 19 to the zero position. To prepare for the first measurement process, the support 7 is moved to the viewer's left until it almost contacts the first yarn gripper 4. Then, the computer 9 is turned on to execute the aforementioned special programming functions.

Figure 2:
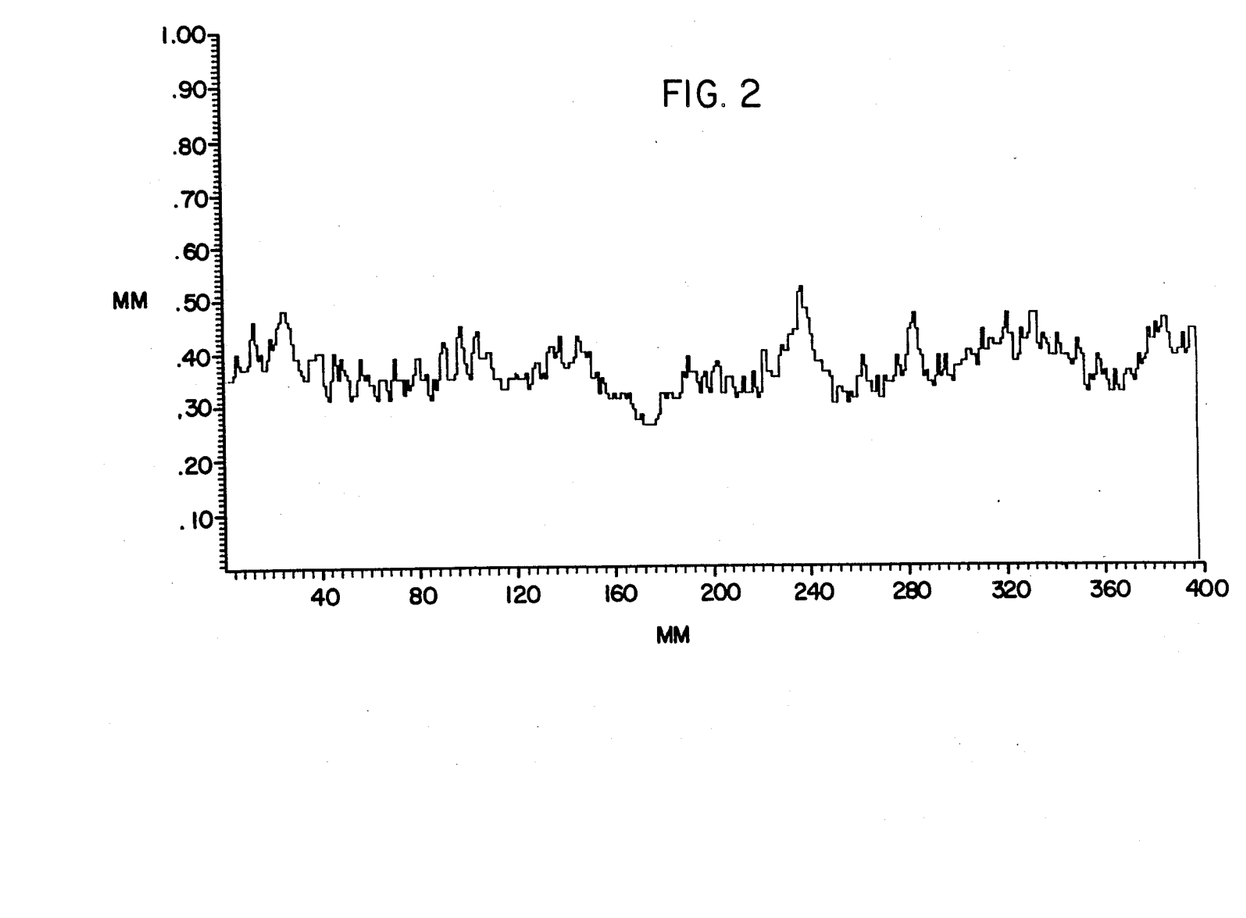
FIG. 2 is a plot of the diameter measurements of a yarn segment from a ring spinning machine using the method of the preferred embodiment of the present invention with the apparatus of FIG. 1.

Next, the motor 68 is activated to rotate the pulley 66 attached thereto in a clockwise direction. The sensor 7 is thus driven to the right along the length of the yarn 3 and the measuring device 71 counts the rotations of the spindle 64 during this movement. When the sensor 7 nears the second yarn gripper 5, the motor 68 is stopped. At each rotation of the spindle 64, the spindle rotation counter 72 sends a register signal to the computer 9. Since the screw thread pitch of the spindle 64 is one millimeter, the diameter measurements along the length of the yarn 3 occur at one millimeter intervals. These diameter measurements, which can be displayed on the monitor 10 or printed by the printer 11, are represented by the plot shown in FIG. 2. The step-wise plot shows the measured yarn diameter over a length of approximately four hundred millimeters.

To prepare for the second measurement process, the yarn segment 3 is first released from its already existing twist orientation. As shown in FIG. 1, the yarn 3 is an S-twisted yarn. To untwist this yarn, the motor 52 is activated to rotate the pulley 51 in a counterclockwise direction. Accordingly, the second yarn gripper 5, through its connection to the pulley 49 by the shaft 46, is also rotated in a counterclockwise direction so that the yarn 3 is untwisted and gradually lengthens. During this untwisting process, the pointer 19 moves slowly to the left, in a counterclockwise direction, and the arcuate strip 38 gradually covers the photocell 39. The extent to which the photocell 39 is covered is a measure of the lengthening of the yarn segment 3 and this measurement is recorded by the computer 9. The movement of the pointer 19 to the left becomes gradually slower until it eventually comes to a stop. At this point, the yarn 3 has been released from its pre-existing twist. If desired, the motor 52 can be allowed to continue running to induce a counter-twisting to the yarn 3 and then the motor 52 can be reversed so that the counter-twisting is untwisted, thereby insuring that the yarn 3 is in its fully released position. The number of pre-existing twists of the yarn 3 can now be read from the scale 43. This number is also stored in the computer 9.

Figure 3:
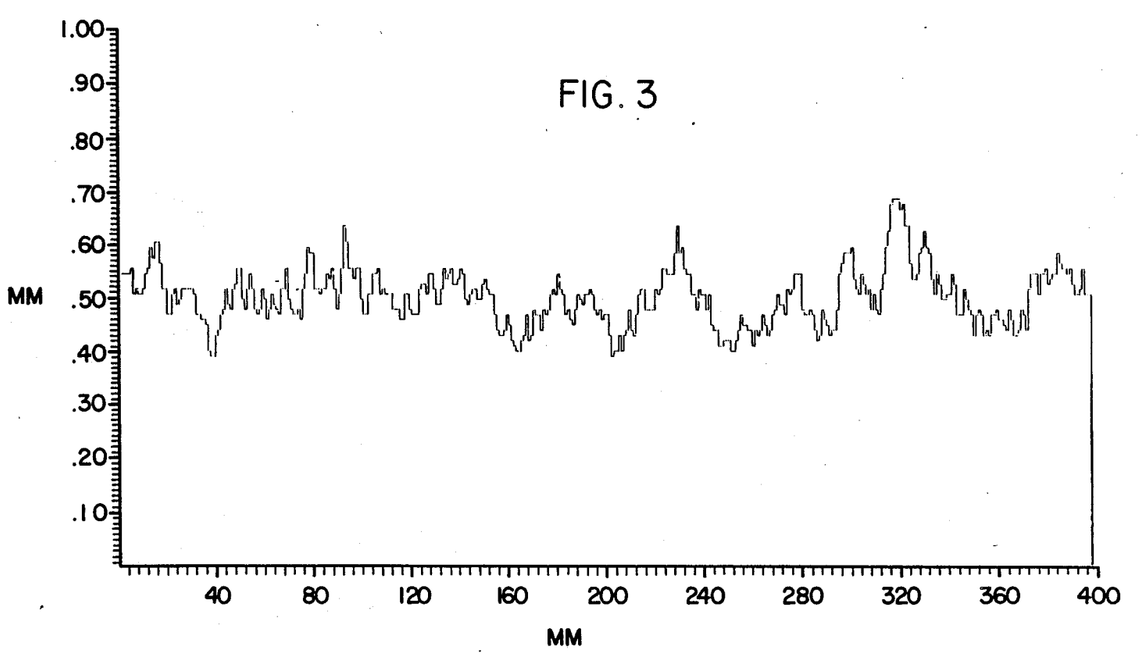
FIG. 3 is a plot of the diameter measurements of the same yarn segment as in FIG. 2 after the removal of the twist already present from its handling in the ring spinning machine.
Figure 4:
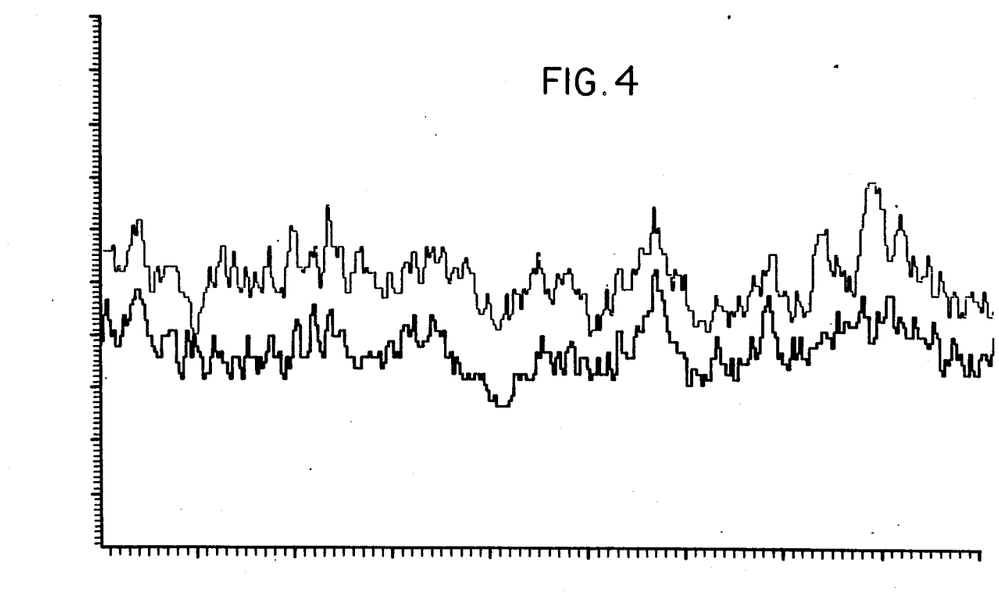
FIG. 4 is a plot of the diameter measurements of FIGS. 2 and 3 on the same coordinate system.

To start the second measuring process, the sensor 7 is returned to its position adjacent the first yarn gripper 4. The second measuring process proceeds basically in the same manner as the first measuring process with the resultant plot of the yarn diameter measured at one millimeter intervals being shown in FIG. 3. As the comparison of the plots of FIGS. 2 and 3 in FIG. 4 shows, the fully released yarn 3 has a greater diameter.

While the first and second measuring processes have been described with respect to the measurement of the yarn diameter, the computer 9 can be programmed to calculate and display a plot of the average yarn diameter values. Also, the deviations of the individual yarn diameter plots from the average yarn diameter plot can be calculated and displayed. Additionally, the change in length of the yarn 3 which occurs in the course of the two measuring processes can be calculated and displayed. This change of length can be compared with an average value to determine the characteristics of the particular yarn segment 3.

The computer 9 can also be programmed to align the plot of yarn diameter values recorded during the second measuring process with the values recorded during the first measuring process. Since the yarn segment 3 is lengthened before the second measuring process, the cross sections of the yarn which were measured at the one millimeter intervals during the first measuring process are offset slightly in the yarn lengthening direction. However, computer 9 can be programmed to align the values obtained for each cross section from both measuring processes so that these values are readable one over the other on a single chart, as shown in FIG. 4. Thus, the plot of yarn diameter values taken during the second measuring process, shown in the lighter, upper line of FIG. 4, corresponds to the plot in FIG. 3 except that it is slightly compressed so that the values for each cross section from the two measuring processes are vertically aligned. FIG. 4 clearly shows that, while the two plots of values may touch at a few positions, in no case do they overlap and this is characteristic of a yarn spun on a ring spinning machine.

The computer 9 can also be adapted to optically or graphically display the diameter or thickness plots, the number and positions of the overlapping of the various plots and the measurements and other characteristics of the yarn to which the overlapping plot portions correspond. In this way, the apparatus of the present invention is especially helpful in investigating the characteristics of open spun yarn.

Figure 5:
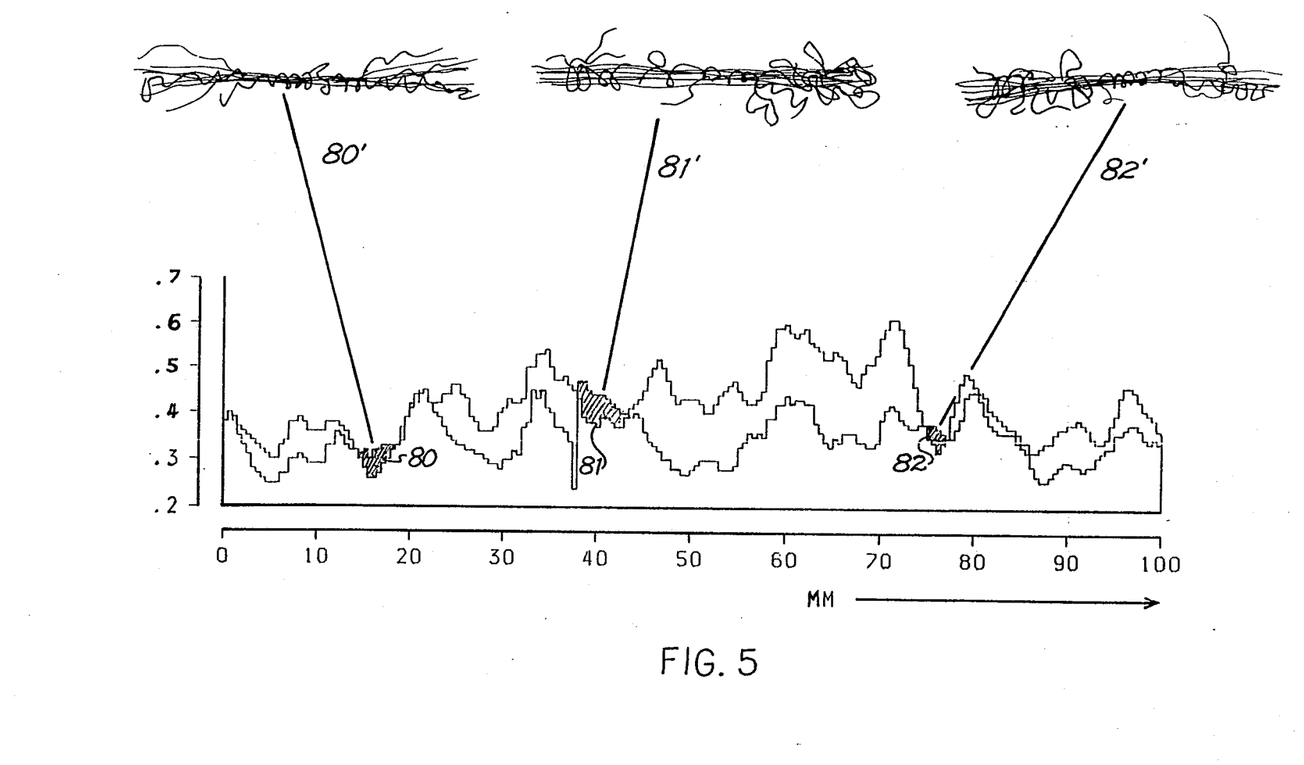
FIG. 5 is a plot of two series of diameter measurements conducted on another segment of yarn and showing the yarn in enlargement in three diagrams, each diagram corresponding to the indicated portion of the diameter measurement plots.

FIG. 5 shows the measurements of an open spun yarn segment. The bottom plot shows the results of the first measuring process while the upper plot shows the results of the second measuring process. As shown in the cross hatched portions 80, 81 and 82, the two plots intersect in several places. An enlarged photograph of the portion of the yarn having the diameters whose values overlap in regions 80, 81 and 82 are labeled as 80', 81' and 82', respectively. The photographs of the yarn portions show that the yarn is encircled by wrapper fibers. In the regions of these wrapper fibers, a tightening of the yarn occurs during the release of the yarn from its pre-existing twist which is evidenced by a counter-twisting of the wrapper fibers which are strengthened by reverse twisting. The width and length of the constrictions can be immediately seen upon viewing the plots of the two series of values from the two measuring processes. The values can also be numerically displayed.

The measuring protocol can also be modified such as, for example, by conducting a third measuring process after the yarn 3 has received a number of twistings following the second measuring process. In this respect, additional comparisons between the values can be made so that the data provided by the measuring processes is even more helpful.

The validity and reliability of the comparison data can be strengthened if several yarn segments of the same batch are subjected to the measuring processes.

In accordance with the present invention, it is possible to use a yarn sensor, such as that shown in FIG. 1, which can be moved along the entire yarn length. Such a sensor could immediately provide an average value for the yarn diameter or thickness. However, depending on the apparatus, information about small details such as, for example, constriction points may not be obtainable. Such a sensor would be most suitable for yarn which is not subject to such constrictions.

It will therefore be readily understood by those persons skilled in the art that the present invention is susceptible of a broad utility and application. Many embodiments and adaptions of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. Method for measuring and testing of staple fiber yarn, comprising:
    measuring the diameter of a staple fiber yarn segment having a predetermined twist;
    manipulating said segment to change the twist thereof; re-measuring the diameter of said segment after said manipulating; and
    comparing the measured diameters to determine characteristics of said segment.

2. Method for measuring the diameter of staple fiber yarn according to claim 1 and characterized further in that said re-measuring the diameter of said segment includes applying a predetermined axial tension to said segment.

3. Method for measuring and testing staple fiber yarn according to claims 1 or 2 and characterized further in that said manipulating said segment includes changing the twist in said segment.

4. Method for measuring and testing staple fiber yarn according to claim 1 and characterized further by further manipulating said segment to change the twist thereof after said re-measuring the diameter of said segment and measuring the diameter of said segment after said further manipulating said segment.

5. Method for measuring staple fiber yarn according to claims 1 or 2 and characterized further in that measuring the diameter of said segment and re-measuring the diameter of said segment each include subjecting said segment to a predetermined tension during the measuring thereof.

6. Method for measuring and testing staple fiber yarn according to claim 4 and characterized further in that said measuring the diameter of said segment, re-measuring the diameter of said segment and measuring the diameter of said segment after said of further manipulating said segment each include subjecting said segment to a predetermined tension during the measuring thereof.

7. Method for measuring and testing staple fiber yarn according to claims 1 or 2 and characterized further in that said manipulating said segment includes substantially fully untwisting said segment and said re-measuring the diameter of said segment includes re-measuring the diameter of said segment after said segment is substantially fully untwisted.

8. Method for measuring and testing staple fiber yarn according to claim 7 and characterized further by recording the number of twists or counter-twists imparted to said segment by said manipulating and recording the change in length of said segment during said manipulating thereof.

9. Method for measuring and testing staple fiber yarn according to claim 8 and characterized further in that said measuring the diameter of said segment and re-measuring the diameter of said segment include measuring the diameter of said segment at intervals in the range of approximately 0.5 to 1 millimeter along the length of said segment.

10. Method for measuring and testing staple fiber yarn according to claim 9 and characterized further by classifying said segment as yarn with wrapper fibers if the diameter of said segment at various axial positions has decreased following the manipulation of said segment to untwist it.

11. Method for measuring and testing staple fiber yarn according to claim 10 and characterized further in that said classifying includes calculating the length of the portions of said segment having diameters which are substantially unchanged after said manipulating said segment.

12. Apparatus for measuring staple fiber yarns, comprising:
 means for measuring the diameter of a staple fiber yarn having a predetermined twist;
 means for manipulating said segment to change the twist thereof;
 means for re-measuring the diameter of said segment after manipulation thereof; and
 means for comparing the measured diameters to determine characteristics of said segment.

13. Apparatus according to claim 12 and characterized further in that said means for measuring the diameter of said segment includes means for applying a predetermined axial tension to said segment.

14. Apparatus according to claims 12 or 13 and characterized further in that said means for manipulating said segment includes means for changing the twist in said segment.

15. Apparatus according to claim 12 and characterized further by means for further manipulating said segment to change the twist thereof after said segment has been re-measured and means for measuring the diameter of said segment after said segment has been further manipulated.

16. Apparatus according to claims 12 or 13 and characterized further in that said means for measuring the diameter of said segment and said means for re-measuring the diameter of said segment each include means for subjecting said segment to a predetermined tension during the measuring thereof.

17. Apparatus according to claim 15 and characterized further in that said means for measuring the diameter of said segment, said means for re-measuring the diameter of said segment and said means for measuring the diameter of said segment after said segment has been further manipulated each include means for subjecting said segment to a predetermined tension during the measuring thereof.

18. Apparatus according to claims 12 or 13 and characterized further in that said means for manipulating said segment includes means for substantially fully untwisting said segment and said means for re-measuring the diameter of said segment includes means for re-measuring the diameter of said segment after said segment is substantially fully untwisted.

19. Apparatus according to claim 18 and characterized further by means for recording the number of twists or counter-twists imparted to said segment by said means for manipulating said segment and means for recording the change in length of said segment during manipulation thereof.

20. Apparatus for measuring a staple fiber yarn segment, comprising:
 means for gripping one end of the segment;
 means for gripping the other end of the segment;
 means for rotating one of said segment ends about the segment axis; and
 means for measuring the diameter of the segment at intervals along its length between said gripping means.

21. Apparatus according to claim 20 and characterized further by means for applying tension to one of said segment ends.

22. Apparatus for measuring and testing a staple fiber yarn segment according to claims 20 or 21 and characterized further by a computer for storing and displaying measurement values provided by said means for measuring.

23. Apparatus for measuring and testing a staple fiber yarn segment according to claims 20 or 21 and characterized further by means for indicating a change in length of the segment resulting from rotation of said segment by said rotating means and means for indicating the number of rotations of said segment by said means for rotating.

24. Apparatus for measuring and testing a staple fiber yarn segment according to claims 20 or 21 and characterized further in that said means for measuring includes means for sensing the diameter of the segment at intervals along its length, means for moving said sensing means axially along the segment, and means for indicating the axial interval of sensing.

25. Apparatus for measuring and testing a staple fiber yarn segment according to claim 24 and charactized further in that said means for moving said sensing means includes a guide member positioned parallel to the segment, said sensing means being coupled to and movable along said guide member, a rotating shaft rotatably coupled to said sensing means and means coupled to said sensing means for converting the rotation of said rotating shaft to translational movement of said sensing means along said guide member and said indicating means includes means coupled to said rotating shaft for indicating the number of rotations of said shaft, whereby the number of shaft rotations is proportional to the axial distance traveled by said sensing means.

26. Apparatus for measuring and testing a staple fiber yarn segment according to claim 22 and characterized further in that said computer includes means for displaying the segment length, the change of length of the segment, and other measured parameters of the segment.

* * * * *